US008448287B2

(12) United States Patent
Ponzini et al.

(10) Patent No.: US 8,448,287 B2
(45) Date of Patent: May 28, 2013

(54) REPLACEABLE TOOTHBRUSH HEAD (75) Inventors: Eligio Ponzini, Milan (IT); Giulio Ponzini, Milan (IT); Fabrizio Pizzi, Lazzate (IT); Hlynur Vagn Atlason, New York City, NY (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/183,417

(22) Filed: Jul. 14, 2011

(65) Prior Publication Data
US 2012/0096665 A1    Apr. 26, 2012

Related U.S. Application Data (63) Continuation-in-part of application No. 29/377,588, filed on Oct. 22, 2010.

(51) Int. Cl.
*A46B 7/04* (2006.01)
(52) U.S. Cl.
USPC ........................................ 15/176.1; 15/176.6
(58) Field of Classification Search
USPC ............ 15/167.1, 176.1, 176.2, 176.3, 176.4, 15/176.5, 176.6, 202
See application file for complete search history.

(56) References Cited

U.S. PATENT DOCUMENTS

| 914,501 | A | | 3/1909 | McEachern |
| 959,574 | A | | 5/1910 | Moore |
| 993,617 | A | * | 5/1911 | Pokorney ..................... 15/176.5 |
| 1,091,209 | A | | 3/1914 | Gates |
| 1,241,881 | A | | 10/1917 | Picard |
| 1,271,252 | A | | 7/1918 | Wilson |
| 1,329,980 | A | | 2/1920 | Laudiero |
| 1,360,292 | A | | 11/1920 | Hartman |
| 1,364,996 | A | | 1/1921 | Jordan |
| 1,407,214 | A | * | 2/1922 | Osborn ....................... 15/176.6 |
| 1,414,886 | A | | 5/1922 | Matsunaga |
| 1,415,898 | A | | 5/1922 | Rost |
| 1,435,641 | A | | 11/1922 | Hines |
| 1,497,495 | A | | 6/1924 | Fincke |
| 1,518,341 | A | | 12/1924 | Mendoza |

(Continued)

FOREIGN PATENT DOCUMENTS

| DE | 9109625.1 | 10/1991 |
| EP | 0704179 | 4/1996 |

(Continued)

OTHER PUBLICATIONS

Tech Light 3 Photos, ca. Jan. 2010.

(Continued)

*Primary Examiner* — Monica Carter
*Assistant Examiner* — Michael Jennings (57) ABSTRACT

A toothbrush with a replaceable head formed to permit ready removal and attachment preferably without the use of a tool. The replaceable toothbrush head may advantageously be formed for coupling with a power toothbrush, particularly, a power toothbrush with a power element that protrudes from the toothbrush head. The replaceable toothbrush head thus preferably is formed to accommodate the power element. In a preferred embodiment, the replaceable toothbrush head is rotated about a rotation axis into engagement with the head of the toothbrush main unit. The replaceable toothbrush head may be moved axially along the rotation axis for alignment with an alignment axis. Preferably, the replaceable toothbrush head is moved axially into engagement with the power element for alignment for coupling with the toothbrush main unit.

20 Claims, 3 Drawing Sheets

U.S. PATENT DOCUMENTS

| | | | |
|---|---|---|---|
| 1,567,507 A | 12/1925 | Howard | |
| 1,625,537 A | 4/1927 | Gullickson | |
| 1,664,797 A | 4/1928 | Stone | |
| 1,701,030 A | 2/1929 | Collins | |
| 1,704,564 A | 3/1929 | Friedland | |
| 1,705,109 A | 3/1929 | Essbach | |
| 1,717,125 A | 6/1929 | Spitz | |
| 1,750,500 A | 3/1930 | Weisz | |
| 1,800,993 A | 4/1931 | Funk | |
| 1,908,510 A * | 5/1933 | Dodson | 15/176.4 |
| 1,908,511 A | 5/1933 | Dodson | |
| 1,932,878 A | 10/1933 | Akizawa | |
| 1,939,001 A | 12/1933 | Doll | |
| 1,944,797 A | 1/1934 | McElwain | |
| 2,005,337 A | 6/1935 | Doll | |
| 2,159,914 A | 5/1939 | Tweedale | |
| 2,225,331 A | 12/1940 | Campbell | |
| 2,290,357 A | 7/1942 | Richenbacher | |
| 2,326,632 A | 8/1943 | Friedman | |
| 2,362,159 A | 11/1944 | Rickenbacher | |
| 2,618,801 A | 11/1952 | Hibbs | |
| 2,668,973 A | 2/1954 | Glaza et al. | |
| 2,675,573 A * | 4/1954 | Strong | 15/176.4 |
| 2,706,825 A | 4/1955 | Blakeman | |
| 2,864,111 A | 12/1958 | Rotceig | |
| 2,976,554 A | 3/1961 | Hromoko et al. | |
| 3,008,165 A | 11/1961 | Scholl | |
| 3,065,480 A | 11/1962 | Sexton | |
| 3,103,680 A | 9/1963 | Krichmar | |
| 3,271,805 A | 9/1966 | Sawyer | |
| 4,020,521 A | 5/1977 | Velasquez | |
| 4,118,824 A | 10/1978 | Clement, Jr. | |
| 4,128,910 A | 12/1978 | Nakata et al. | |
| 4,227,276 A | 10/1980 | Ginsburg et al. | |
| 4,362,174 A | 12/1982 | Baker et al. | |
| 4,399,582 A | 8/1983 | Ernest et al. | |
| 4,403,623 A | 9/1983 | Mark | |
| 4,409,701 A | 10/1983 | Perches | |
| 4,411,041 A | 10/1983 | Braga | |
| D282,316 S | 1/1986 | Herzfeld | |
| 4,575,894 A | 3/1986 | Stevens et al. | |
| 585,358 A | 6/1987 | Gould | |
| 4,683,604 A | 8/1987 | Rueb | |
| 4,890,349 A | 1/1990 | Nitzsche | |
| 5,120,225 A * | 6/1992 | Amit | 433/216 |
| 5,224,234 A | 7/1993 | Arsenault et al. | |
| 5,228,166 A | 7/1993 | Gomez | |
| 5,242,235 A | 9/1993 | Li | |
| 5,247,716 A | 9/1993 | Bock | |
| 5,247,718 A | 9/1993 | Victorian | |
| 5,269,038 A | 12/1993 | Bradley | |
| 5,396,679 A | 3/1995 | Brown et al. | |
| 5,398,366 A | 3/1995 | Bradley | |
| D357,809 S | 5/1995 | Brown et al. | |
| 5,412,831 A * | 5/1995 | Mongelluzzo | 15/167.1 |
| 5,435,033 A | 7/1995 | Millner | |
| 5,481,775 A | 1/1996 | Gentile et al. | |
| 5,491,866 A | 2/1996 | Simonds | |
| 5,511,276 A | 4/1996 | Lee | |
| 5,528,786 A | 6/1996 | Porat et al. | |
| 5,555,590 A | 9/1996 | Blum et al. | |
| 5,737,792 A | 4/1998 | Quigless | |
| 5,839,148 A | 11/1998 | Volpenhein | |
| 5,864,915 A * | 2/1999 | Ra | 15/167.1 |
| 6,079,075 A | 6/2000 | Velez-Juan | |
| 6,138,316 A | 10/2000 | Weihrauch | |
| 6,170,111 B1 | 1/2001 | Rueb et al. | |
| 6,237,183 B1 | 5/2001 | Fischer | |
| 6,345,406 B1 | 2/2002 | Dodd | |
| 6,360,398 B1 | 3/2002 | Wiegner et al. | |
| 6,408,473 B1 | 6/2002 | Kessler | |
| 6,434,777 B1 | 8/2002 | Sutton | |
| 6,463,620 B2 | 10/2002 | Busha | |
| 6,487,748 B1 * | 12/2002 | Dardar et al. | 15/167.1 |
| 6,536,068 B1 | 3/2003 | Yang et al. | |
| 6,550,095 B2 | 4/2003 | Hawkins et al. | |
| 6,752,627 B2 | 6/2004 | Lin | |
| 6,775,875 B2 | 8/2004 | Ornelas et al. | |
| 7,329,273 B2 | 2/2008 | Altshuler et al. | |
| 7,329,274 B2 | 2/2008 | Altshuler et al. | |
| 7,354,448 B2 | 4/2008 | Altshuler et al. | |
| 7,422,598 B2 | 9/2008 | Altshuler et al. | |
| 7,549,186 B2 * | 6/2009 | Geiberger | 15/167.1 |
| 7,599,506 B2 | 10/2009 | Filo et al. | |
| 7,913,347 B2 * | 3/2011 | Wong | 15/172 |
| 2002/0178524 A1 | 12/2002 | Hawkins et al. | |
| 2002/0184724 A1 | 12/2002 | Saar | |
| 2003/0074755 A1 | 4/2003 | Ale et al. | |
| 2003/0115705 A1 | 6/2003 | Aoyama | |
| 2003/0172483 A1 | 9/2003 | Davis | |
| 2004/0194238 A1 | 10/2004 | Letendre | |
| 2005/0066459 A1 | 3/2005 | Pinyayev et al. | |
| 2006/0080797 A1 | 4/2006 | Yu | |
| 2006/0085932 A1 | 4/2006 | Santos | |
| 2006/0123955 A1 | 6/2006 | Cho | |
| 2006/0236483 A1 | 10/2006 | Koi | |
| 2007/0136968 A1 * | 6/2007 | Lee | 15/167.1 |
| 2007/0283519 A1 | 12/2007 | Moss | |
| 2008/0087568 A1 * | 4/2008 | Jabri | 206/570 |
| 2008/0131844 A1 * | 6/2008 | Taylor | 433/216 |
| 2008/0172812 A1 | 7/2008 | Dean | |
| 2008/0184511 A1 | 8/2008 | Brown et al. | |
| 2008/0271271 A1 * | 11/2008 | Chan | 15/22.2 |
| 2008/0276393 A1 * | 11/2008 | Russell et al. | 15/105 |
| 2008/0301892 A1 | 12/2008 | Blair | |
| 2009/0038091 A1 * | 2/2009 | Denney et al. | 15/28 |
| 2009/0083924 A1 | 4/2009 | Shepherd et al. | |
| 2009/0091178 A1 * | 4/2009 | Waguespack et al. | 300/21 |
| 2009/0113650 A1 | 5/2009 | Flek, Jr. et al. | |
| 2009/0126132 A1 | 5/2009 | Hafliger et al. | |
| 2010/0178252 A1 | 7/2010 | Sagel et al. | |

FOREIGN PATENT DOCUMENTS

| | | |
|---|---|---|
| FR | 2559656 | 2/1984 |
| GB | 2035073 | 6/1980 |
| JP | 6304020 | 11/1994 |
| JP | 6304021 | 11/1994 |
| JP | 6304022 | 11/1994 |
| JP | 2003199622 | 7/2003 |
| WO | 9801055 | 1/1998 |
| WO | 03073958 | 9/2003 |

OTHER PUBLICATIONS

Cross Action 5 Photos, ca. Jan. 2010.

* cited by examiner

REPLACEABLE TOOTHBRUSH HEAD

CROSS-REFERENCE TO RELATED APPLICATION

The present application is a continuation-in-part of and claims the benefit of the earlier filing date of U.S. design patent application No. 29/377,588, filed Oct. 22, 2010, which application is hereby incorporated by reference herein in its entirety

FIELD OF THE INVENTION

The present invention relates to a replaceable head for a toothbrush. More particularly, the present invention relates to a replaceable toothbrush head that is easy to remove from and to couple to a toothbrush main unit without the need for special tools.

BACKGROUND OF THE INVENTION

Toothbrushes have handles that are generally formed of a relatively durable material that lasts longer than the brushing bristles. In fact, the American Dental Association recommends replacing toothbrushes every 3-4 months (or even more frequently) because the bristles typically become frayed and worn with use, resulting in a decrease in cleaning effectiveness. In addition, improved oral hygiene is promoted through toothbrush replacement. Since germs may breed in the bristle section, regular replacement of toothbrushes (preferably at least every 3-4 months) greatly reduces germ accumulation and transmission from bacteria-encrusted bristles.

A cost-effective alternative to purchasing a new toothbrush is the replacement of only the cleaning portion of the brush. It may be particularly desirable to replace only the head or brush sections if, for instance, the handle or gripping section is costly (e.g., made from an expensive material), or if the handle or gripping portion has an ornamental design (which the user would like to keep using).

One type of toothbrush with an expensive handle is a powered or electric toothbrush. Powered or electric toothbrushes (hereinafter, "power toothbrushes" for the sake of convenience, without intent to limit) have been available for some time, and are becoming increasingly popular with both adults and children. Power toothbrushes have advantages over manual (non-powered) toothbrushes in that they may impart movement to the bristles at much higher speeds than possible manually. Such toothbrushes also may impart different types and directions of motion, and/or other functionalities. The various motions, generally in combination with manual movement of toothbrush by the user, are commonly viewed as providing superior cleaning than manual toothbrushes.

Known power toothbrushes include a brush head with a bristle carrier portion that moves (rotates, oscillates, vibrates, etc.) in some manner so as to clean the teeth. The bristles, which typically comprise bristle tufts, are generally uniform with one end fixed into the bristle carrier portion and the other end free to contact the surface of the teeth while brushing (the free, cleaning ends of the bristles). The free ends of the various tufts present a surface envelope that is capable of some deformation when the bristles bend. When in contact with the tooth surface to be brushed, the bristles may deform so that the surface envelope tends to conform to the complex surface of the teeth.

Power toothbrushes which emit light or generate other emissions from one or more electrically powered elements disposed in the head of the toothbrush, or other area remote from the head, are also known. Emissions from the electrically powered elements in the head of the toothbrush may be transmitted from elements such as light-emitting diodes (LEDs) or fiber optics. Examples of such toothbrushes are described, for example in United States published patent application 2010/0178252 to Sagel et al., entitled "Products and Methods for Disclosing Conditions in the Oral Cavity," and assigned to The Procter & Gamble Company Intellectual Property Division; United States published patent application 2005/0066459 to Pinyayev et al., entitled "Electric Toothbrushes and Replaceable Components," and assigned to The Procter & Gamble Company Intellectual Property Division; U.S. Pat. No. 7,422,598 to Altshuler et al., entitled "Multi-Wavelength Oral Phototherapy Applicator," and assigned to Palmoar Medical Technologies, Inc.; U.S. Pat. No. 7,354,448 to Altshuler et al., entitled "Dental Phototherapy Methods and Compositions," and assigned to Palmoar Medical Technologies, Inc.; U.S. Pat. No. 7,329,274 to Altshuler et al., entitled "Conforming Oral Phototherapy Applicator," and assigned to Palmoar Medical Technologies, Inc.; U.S. Pat. No. 7,329,273 to Altshuler et al., entitled "Tissue Penetrating Oral Phototherapy Applicator," and assigned to Palomar Medical Technologies, Inc. The electrically powered element can be disposed on or in the head of the toothbrush. However, the power element must be of a size and placement such that space remains for bristles and the mechanical components of the power toothbrush. Mechanical components used to convey motion to the bristles typically consume much of the space available within the head and neck of the toothbrush. Increasing the size of the head and/or handle of the toothbrush to increase space for including the electrically powered element results in a toothbrush that is commonly felt to be too large to effectively and comfortably clean the surfaces of the oral cavity, and is generally avoided in most designs.

As noted above, it is desirable to form a power toothbrush with a replaceable head as a cost-effective alternative to the purchase of a new power toothbrush when the bristles are worn and/or softened and do not perform as effectively as desired. Preferably, the main unit of the power toothbrush may be used well after the bristles of the first toothbrush head have been worn out, and toothbrush heads may be replaced as needed while still using the original main unit. In power toothbrushes with energy sources disposed in the head, the replaceable head may be formed to contain the energy source. However, a more cost-effective alternative is a replaceable head that accommodates an energy source that remains coupled to the main unit (rather than remaining with the replaceable head). Cost savings are realized by not replacing the energy source and by the reduction of material needed in the replaceable head. Examples of such replaceable heads are shown in the above-noted United States patent publications 2010/0178252 and 2005/0066459 and in the UltraBlu™ toothbrush sold by TechLight Systems, Inc., of Florida (see http://www.ultrablu.net/).

Another desire for a replaceable head is ease of replacement. Means of attachment in prior art replaceable heads include such connections as interference fits, and snap-on, screw-on, and dovetail connections. Ease of replacement may be complicated in replaceable heads that accommodate energy source coupled to the main unit because of the need to couple the replaceable head with the energy source in a particular manner, and because the energy source may interfere with certain movements necessary to couple the replaceable head with the main unit. For instance, an energy source as shown in the above-noted United States patent publications protrudes from the main unit so that a dovetail connection requiring sliding of the replaceable head with respect to the head of the main unit is not feasible. It would be desirable to provide a replaceable head for a power toothbrush that accommodates the energy source disposed on the toothbrush head (such that the mechanics of the toothbrush are not interrupted or otherwise compromised) and which also facilitates removal and replacement of the replaceable head.

SUMMARY OF THE INVENTION

In accordance with the principles of the present invention, a replaceable toothbrush head is configured to facilitate removal and replacement. Preferably, the replaceable head also is configured to use less material than used by typical prior art replaceable toothbrush heads. In addition, or alternatively, the replaceable head is preferably configured to accommodate transmission of energy (such as from an energy source) therethrough to apply such energy to a user's teeth as the bristles of the toothbrush head contact and clean the user's teeth.

These and other features and advantages of the present invention will be readily apparent from the following detailed description of the invention, the scope of the invention being set out in the appended claims.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

An exemplary toothbrush 100 having an exemplary toothbrush main unit 110 and an exemplary replaceable head 210 formed in accordance with principles of the present invention is illustrated in FIGS. 1-4. Toothbrush main unit 110 extends along longitudinal axis L and has a proximal end 101 and a distal end 103, with a handle portion 112 at proximal end 101, and a neck portion 114 extending distally towards a head portion 116. Head portion 116 has a head receiver 120 extending along longitudinal axis L and configured to receive a replaceable toothbrush head such as replaceable head 210. In a preferred embodiment, toothbrush 100 is a power toothbrush, and main unit 110 contains the power (mechanical and electro-mechanical and/or electrical) elements thereof. In an even more preferred embodiment, head receiver 120 carries a power element 130 and replaceable head 210 is configured to accommodate power element 130. In the exemplary embodiment of FIGS. 1-4, power element 130 projects above and into replaceable head 210 and replaceable head 210 has an aperture 230 for accommodating power element 130 (which may extend above bristle-carrying surface 214 of bristle carrier 212 of replaceable head 210). Aperture may be a through hole or a recess (blind hole) covering power element 130. However, it will be appreciated that other configurations of power element 130 and replaceable head 210 are within the scope of the present invention.

In the exemplary embodiment of main unit 110 of FIGS. 1-4 with a power element 130 carried by head receiver 120, head receiver 120 preferably is configured to receive a replaceable toothbrush head in a manner that permits power element 130 to remain coupled to main unit 110 while permitting preferably repeated removal and replacement of replaceable heads therefrom and thereto. In the exemplary embodiment of FIGS. 1-4, head receiver 120 has a substantially planar toothbrush-head-receiving surface 122 that permits a substantially planar, plate-like replaceable head (such as replaceable head 210, as described in further detail below) to be coupled thereto in a layered or laminate or sandwiched manner, and preferably coplanar therewith. As such, power element 130 remains connected to and powered by main unit 110, yet is provided in a position for functioning when replaceable head 210 is coupled thereto. In a preferred embodiment, toothbrush-head-receiving-surface 122 preferably has a main unit connector 124 for connecting with a corresponding connector on a replaceable head (such as described in further detail below). In the exemplary embodiment of FIGS. 1-4, main unit connector 124 preferably also includes a main unit alignment element 126 for aligning a replaceable head for connection with main unit connector 124 and main unit 110, in a manner such as described below. In the exemplary embodiment of FIGS. 1-4, main unit alignment element 126 may be in the form of a protruding element. However, other forms of alignment elements (e.g., an optical lens, a teeth-cleaning element, and a toothpaste dispensing element) are within the scope of the present invention. In a preferred embodiment, power element 130 serves a dual function of providing a power function or feature as well as serving as main unit alignment element 126. Because replaceable head 210 is sandwiched together with head receiver 120, the power element of toothbrush 100 (e.g., power element 130) is positioned to function through replaceable head 210. For instance, an aperture 230 may be provided in replaceable head 210 so that power element 130 is unimpeded by replaceable head 210 when coupled to head portion 116 on which power element 130 is provided. If desired, aperture 230 may be shaped and configured to permit power element 130 to extend at least partially therethrough. In the exemplary embodiment of FIGS. 1-4, the inside diameter of aperture 230 preferably is selected to correspond to the outside diameter of main unit alignment element 126.

In accordance with principles of the present invention, replaceable head 210 preferably has a plate-like bristle carrier 212 having a first surface 214 from which a plurality of bristles 215 extend and a second surface 216 opposite first surface 214 having a substantially planar head-receiver-engaging surface 222 for being laid over toothbrush-head-receiving surface 122 on head receiver 120 for engagement therewith in a substantially sandwiched manner such as described above. As used herein, "plate-like" element is intended to mean a thin element having a length and width which are both at least three times the thickness/depth. In a preferred embodiment, a "plate-like" element has a major dimension (extending in the length-width directions) extending predominantly in a single plane. It will be appreciated that, as discussed above, the formation of bristle carrier 212 as a plate-like element permits replaceable head 210 to be layered or sandwiched with head receiver 120 to form a complete toothbrush head that is not unduly bulky for use within a typical user's mouth. The attachment or connection element provided to couple replaceable head 210 with head receiver 120 preferably is designed to minimize the overall head thickness. In a preferred embodiment, replaceable head 210 is designed with a connector configured to fit into a recess in head receiver 120. In addition, a plate-like replaceable head 210 generally is thinner than typical replaceable toothbrush heads, thus requiring less material than required for typical replaceable toothbrush heads.

Moreover, a plate-like replaceable head 210 preferably does not contain any power elements that perform the power function of toothbrush 100 (in the case in which toothbrush 100 is a power toothbrush). Thus, costs of replaceable head 210 are lower than a larger or thicker replaceable head and a replaceable head containing power elements. The minimum thickness of plate-like bristle carrier 212 depends on various factors, such as material type, retention force, manipulability, etc., described in further detail below. In accordance with principles of the present invention, replaceable head 210 is coupled to head receiver 120 in a secure manner so that replaceable head 210 does not inadvertently disengage from head receiver 120, particularly during use of toothbrush 100. In particular, replaceable head 210 preferably is secured to head portion 116 to withstand a removal force (the "attachment/retention force") of at least 3.0 lbs (1.36 kg). Preferably, head receiver 120 and replaceable head 210 have connectors 124, 224, respectively, that may be coupled together to retain head receiver 120 and replaceable head 210 together in a secure manner as required by the typical uses of toothbrush 100. In a preferred embodiment, head-receiver-connector 124 interfits or interlocks or engages or is coupled with (hereinafter "engages" for the sake of convenience, without intent to limit) replaceable-head-connector 224 in a secure, preferably locking, manner. In the embodiment of FIGS. 1-4, such engagement of connectors 124, 224 is achieved by a dovetail-type connection in which head-receiver-connector 124 has at least one and preferably two locking extensions 140a, 140b (collectively, locking extensions 140) and replaceable-head-connector 224 has corresponding locking extensions 240a, 240b (collectively, locking extensions 240) for each head-receiver-connector locking extension 140a, 140b. When locking extensions 140, 240 are engaged together, replaceable head 210 is securely engaged with head receiver 120.

Figure 1:
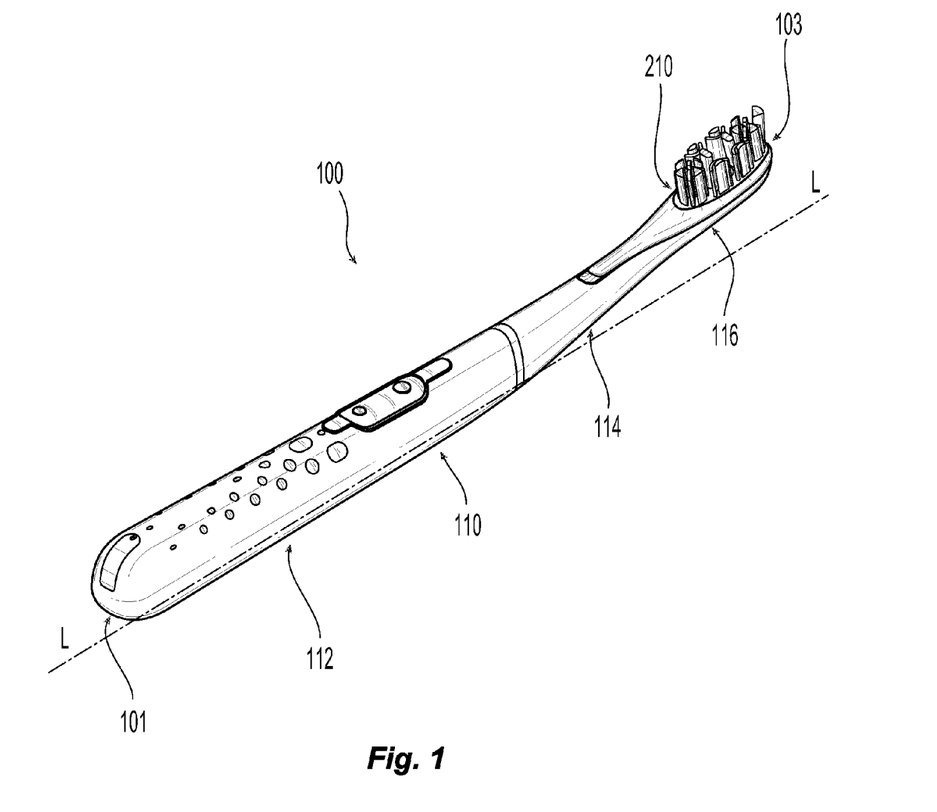
FIG. 1 is a perspective view of an exemplary toothbrush with replaceable head formed in accordance with principles of the present invention.
Figure 2:
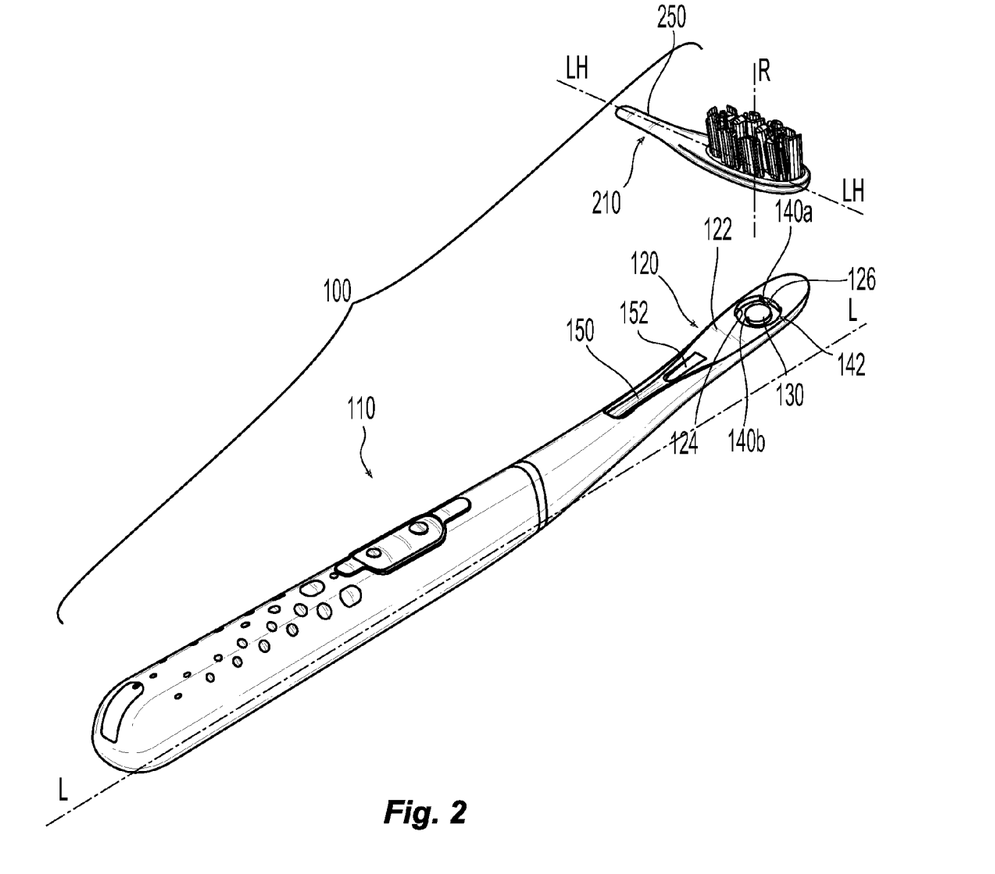
FIG. 2 is an exploded view of the toothbrush of FIG. 1, showing the replaceable head removed from the toothbrush main unit.
Figure 3:
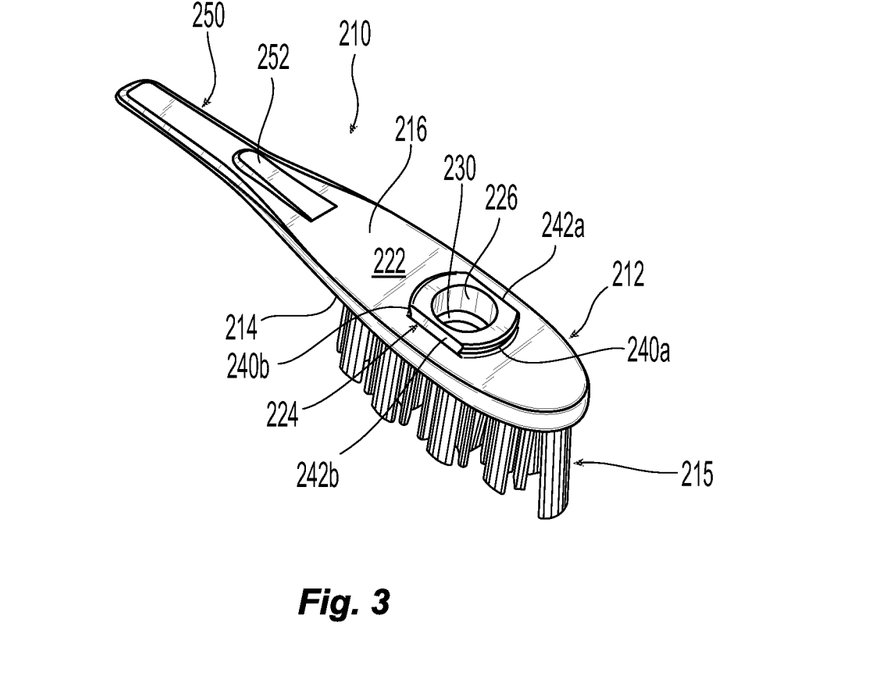
FIG. 3 is a back perspective view of an exemplary replaceable toothbrush head formed in accordance with principles of the present invention.
Figure 4:
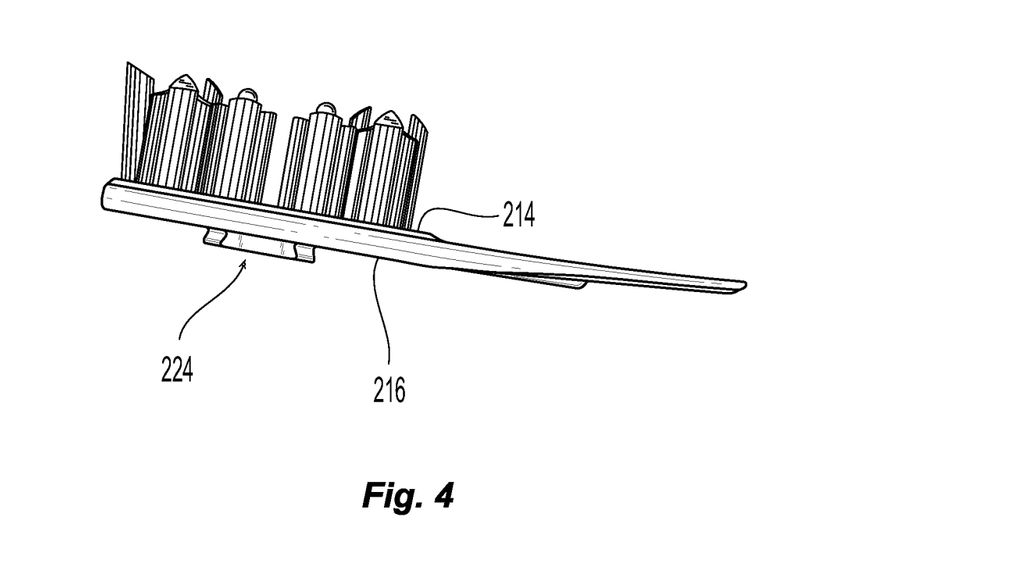
FIG. 4 is a side elevational view of the exemplary replaceable toothbrush head of FIG. 3.

As is typical with dovetail connectors, head-receiver-connector 124 and replaceable-head-connector 224 preferably are moved (e.g., slid or rotated) with respect to each other from an unengaged configuration into an engaged configuration in which connectors 124, 224 secure replaceable head 210 on head receiver 120. Replaceable head 210 preferably has a use position in which replaceable head longitudinal axis LH is substantially aligned with main unit longitudinal axis L. Accordingly, connectors 124, 224 preferably are configured to engage each other when longitudinal axis LH is substantially aligned with main unit longitudinal axis L. To engage replaceable-head-connector 224 with head-receiver-connector 124, replaceable head 210 must be oriented with replaceable head longitudinal axis LH unaligned with main unit longitudinal axis L so that locking extensions 240a, 240b of replaceable-head-connector 224 may be moved under locking extensions 140a, 140b, respectively, of head receiver 120. Replaceable head 210 then is moved, such as by sliding or rotating, to position locking extensions 240a, 240b of replaceable-head-connector 224 under locking extensions 140a, 140b, respectively, of head receiver 120. In the exemplary embodiment of FIGS. 1-4, such movement is a rotational movement about rotation axis R. More particularly, in the exemplary embodiment of FIGS. 1-4, locking extensions 140a, 140b of head-receiver-connector 124 lie substantially opposite each other (although other orientations are within the scope of the present invention). As may be seen in FIG. 2, locking extensions 140a, 140b lie substantially along longitudinal axis L, although other positions with respect to longitudinal axis L are within the scope of the present invention. Likewise, as may be seen in FIGS. 3 and 4, locking extensions 240a, 240b of replaceable-head-connector 224 lie substantially along replaceable head longitudinal axis LH. Replaceable head 210 accordingly is positioned with replaceable head longitudinal axis LH unaligned (preferably transverse to) main unit longitudinal axis L so that locking extensions 240a, 240b of replaceable-head-connector 224 are positioned alongside and unengaged with locking extensions 140a, 140b for movement into engagement therewith. As used herein, "transverse" is to be understood as not aligned, i.e., not 0 degrees or 180 degrees, but not necessarily 90 degrees. Replaceable head 210 is rotated about rotation axis R to move locking extensions 240a, 240b of replaceable-head-connector 224 into engagement with locking extensions 140a, 140b of head-receiver-connector 124, and preferably also to move replaceable head longitudinal axis LH into alignment (most preferably parallel) with main unit longitudinal axis L so that replaceable head 210 is in a proper use position with respect to main unit 110. In the exemplary embodiment, as shown in FIG. 2, replaceable head 210 may be positioned with its longitudinal axis LH substantially transverse to main unit longitudinal axis L to place locking extensions 240a, 240b of replaceable-head-connector 224 in proper position for movement with respect to locking extensions 140a, 140b of head-receiver-connector 124 for engagement therewith. Replaceable head 210 is then rotated about rotation axis R to move locking extensions 240a, 240b of replaceable-head-connector 224 into engagement with locking extensions 140a, 140b of head-receiver-connector 124. To facilitate alignment, each of connectors 124, 224 may be asymmetrical so that they may be engaged together in a limited manner. More particularly, connectors 124, 224 in the exemplary embodiment of FIGS. 1-4 are asymmetrical and substantially elongated along longitudinal axes L, LH, respectively. Accordingly, the relative position in which replaceable head 210 may be placed with respect to head receiver 120 preferably is at least somewhat restricted to facilitate proper alignment of connectors 124, 224 for ready engagement with each other. As may be appreciated with reference to FIG. 3, replaceable-head connector 224 may be elongated along replaceable head longitudinal axis LH with opposite non-locking sides 242a, 242b, and head-receiver connector 124 has widened receiving area 142 to receive the full longitudinal extent of replaceable-head connector 224. Preferably, the other dimensions of head-receiver connector 124 are not sized to accommodate the largest dimension (in the exemplary embodiment, the longitudinal extent) of replaceable-head connector 224 so that connection of replaceable head 210 with head receiver 120 via their respective connectors 124, 224 preferably is restricted to being achieved in the optimal configuration for subsequent engagement with connectors 124, 224 to engage replaceable head 210 securely on head receiver 120. In the embodiment of FIGS. 1-4, opposite non-locking sides 242a, 242b of replaceable-head connector 224 are substantially straight and parallel to each other and the outer periphery of locking extensions 240a, 240b is curved to facilitate initial engagement of replaceable-head connector 224 with head-receiver connector 124, and subsequent rotation of replaceable-head connector 224 with respect to head-receiver connector 124 to engage locking extensions 240 with locking extensions 140. However, it will be appreciated that other shapes and configurations of connectors 124, 224 are within the scope of the present invention.

In a preferred embodiment formed in accordance with principles of the present invention, at least one of replaceable head 210 and head receiver 120 has an alignment element 126, 226 configured to align head receiver 120 and replaceable head 210 for proper engagement with each other, particularly to permit engagement of replaceable-head-connector 224 with head-receiver-connector 124. The at least one alignment element 126, 226 preferably also aligns replaceable head 210 for rotation with respect to head receiver 120 to engage replaceable-head connector 224 with head-receiver connector 124. Provision of at least one alignment element 126, 226, preferably along rotation axis R, is particularly helpful when replaceable head 210 is rotated about rotation axis R for engagement of replaceable-head-connector 224 with head-receiver-connector 124. Preferably, the at least one alignment element 126, 226 permits axially unimpeded engagement of connectors 124, 224 axially along rotation axis R. One or both of alignment elements 126, 226 may extend substantially transverse (and preferably perpendicular to) the surface from which it extends.

In the exemplary embodiment of FIGS. 1-4, a head-receiver alignment element 126 in the form of a protrusion is provided on head receiver 120 and a replaceable-head alignment element 226 in the form of an aperture or recess configured to receive the protruding head-receiver alignment element 126 is provided on replaceable head 210. It will be appreciated that the reverse configuration (head-receiver alignment element 126 being in the form of an aperture and replaceable-head alignment element 226 being in the form of a protrusion) or other configurations of alignment elements 126, 226 are within the scope of the present invention.

In accordance with above-described principles of the present invention, alignment elements 126, 226 may be used to particular advantage in a toothbrush 100 which is a power toothbrush having a power element 130 in head portion 116. In particular, power element 130 may be configured to serve as alignment element 126, and aperture 230 in replaceable head 210 (for accommodating power element 130) may be configured to serve as alignment element 226.

In accordance with a preferred aspect of the present invention, replaceable head 210 preferably may be coupled to head receiver 120 without the need for another component. Most preferably, replaceable head 210 is readily removable from main unit head receiver 120 without the need for a specialized tool. Rather, replaceable head 210 may be manually manipulated relative to head receiver 120 to remove replaceable head 210 from head receiver 120.

In accordance with one aspect of the present invention that need not be applied in conjunction with above-described connectors 124, 224, replaceable head 210 may include an extension or post 250 (hereafter "extension" for the sake of convenience, without intent to limit) configured to facilitate manual manipulation of replaceable head 210 for engagement with or removal from head receiver 120. For instance, exemplary extension 250 of the exemplary embodiment of FIGS. 1-4 extends sufficiently away from bristles 215 for manipulation (e.g., rotation, in the case of connectors 124, 224 in the form of dovetail connectors, particularly in conjunction with an alignment element such as alignment element 126 which interferes with relative lateral sliding of connectors 124, 224 into engagement with each other) of replaceable head 210 with the user's fingers sufficiently distanced from bristles 215 so as not to contact bristles 215. In the embodiment of FIGS. 1-4, extension 250 extends along replaceable-head longitudinal axis LH and preferably is aligned with neck 114 when replaceable head 210 is securely engaged with head receiver 120.

In addition, extension 250 may be configured to assist in maintaining engagement or confirming engagement of replaceable head 210 with head receiver 120. Extension 250 may be configured to fit within a corresponding recess 150 in neck 114. As noted above, it may be desirable to maintain the size of the toothbrush neck 114 under a predetermined size, and preferably to have neck 114 taper smoothly for optimal user comfort when head portion 116 with replaceable head 210 coupled thereto is inserted in the user's mouth during use. Accordingly, recess 150 and extension 250 preferably are dimensioned to fit together to result in a smooth profile (so no sharp edges are presented which may cause discomfort during use of toothbrush 100) as well as a profile within the desired dimensions. Furthermore, as will be appreciated with references to the above-discussions of desired thickness of replaceable head 210, similar considerations are applicable to the thickness of extension 250. The nominal thickness of extension 250 if formed of HH315MO polypropylene (for engagement with a neck 114 formed of polyoxymethylene ("POM")) is approximately 1.6 mm for easy maneuverability to attach replaceable head 210 to head receiver 120, and for sufficient stiffness to snap into recess 150 for a secure fit. The depth of recess 150 preferably is selected to accommodate extension 250 to achieve the desired exterior smooth profile of the resulting neck 114 with extension 250 within recess 150 (e.g., so that no edges or other protrusions are presented which potentially may injure the soft tissue in the user's mouth). Such depth may also be considered to retain extension 250 within recess 150 sufficiently to inhibit unintended lateral movement of extension 250 (such as may occur during use) that would otherwise unseat extension 250 from recess 150. Such configuration is particularly beneficial for maintaining in place a replaceable head 210 that is engaged with head receiver 120 by relative rotation therewith.

Additional features may be provided to inhibit detachment of replaceable head 210 from head receiver 120. In the exemplary embodiment of FIGS. 1-4, locking detent 252 is provided on the underside of extension 250 (the side facing recess 150) for engagement with locking recess 152 in recess 150. Positioning of locking detent 252 in locking recess 152 provides a more secure seating of extension 250 within recess 150, thereby further limiting the possibility of inadvertent movement of extension 250 out of recess 150. The combination of detent 252 and locking recess 152 provides a secondary lock and also further aides in aligning replaceable head 210 for secure engagement with head receiver 120. In addition, detent 252 and locking recess 152 may be formed to provide an audible cue that extension 250 is properly in place and aligned with respect to neck 114. Such audible cue may be achieved by a combination of the depth of detent 252, the thickness of extension 250 itself, and the material from which both are formed. In an extension 250 formed of HH315MO polypropylene for engagement with a neck 114 formed of POM, detent 252 preferably has a nominal height or depth of approximately 1.0 mm for the desired secure engagement of extension 250 with neck 114, the desired resistance to movement (particularly rotation) of extension 250 with respect to neck 114 during brushing, and to provide the audible cue that extension 250 is securely engaged within recess 150 and detent 252 is securely engaged in locking recess 152.

As noted above, it is generally considered desirable to minimize the thickness of neck 114 and head portion 116 with replaceable head 210 attached to head receiver 210 for a comfortable fit in the user's mouth during use. It will be appreciated that "comfort" is generally subjective, and, therefore, "a comfortable fit" is preferably determined based on consumer testing, with a majority of consumers rating the fit to be comfortable. Accordingly, it is generally desirable for replaceable head 210 to be as thin as possible, as described above. Another factor influencing the thickness of replaceable head 210 is the ability to endure sufficient retention force and to withstand a pull out force within the range exhibited during typical use so that replaceable head 210 cannot be easily unintentionally extracted off head retainer 120. As described above, replaceable head 210 preferably is secured to head portion 116 to withstand an attachment/retention force of at least about 3.0 lbs. In other words, replaceable head 210 should not be so thin as to give up retention force and to permit flexing thereof when force is applied thereto (pulling replaceable head 210 away from head receiver 120) to result in undesired and/or improper removal of replaceable head 210 from head receiver 120. In addition, replaceable head 210 should not be so thin as to not retain its shape independently (e.g., replaceable head 210 preferably is not so thin as to flex on its own, as a result of gravity). However, a certain degree of flexibility of replaceable head 210 may be desired so that replaceable head 210 may be manipulated without tending to crack or to lock or bind with head receiver 120. Thus, selection of the material from which replaceable head 210 is formed is also important for the desired functionality of replaceable head 210. For instance, because main unit 110 is intended to outlast replaceable head 210 (which preferably is to be replaced on a regular basis), the material of replaceable head 210 is preferably softer than the material of main unit 110 so that replaceable head 210 will tend to wear out before main unit 110 does. Also, a replaceable head 210 that is softer than main unit 110 typically is perceived by a user as more comfortable to put on and take off from head portion 116.

Typically, it is desirable to form main unit 110 from a relatively stiffer, hard material for durability and repeated use with successive replacement of replaceable heads 210. Of course, a certain degree of flexibility (typically virtually imperceptible during use) of handle 112 and preferably also neck 114 is desirable for comfort during use. It will be appreciated that the degree of flexibility of neck 114 preferably is determined based on the functionality of toothbrush 100. For instance, if toothbrush 100 is a power toothbrush with a vibrating head, neck 114 should not be so flexible that it flexes with vibration of head portion 116; sufficient vibration from the power elements (typically housed in handle 112) should be transferred to head portion 116, without unduly being absorbed by neck 114 (which would occur if neck 114 is made of a more flexible material). The head vibration is generally considered important to clinical efficacy, and also to consumer perception and low noise during use.

It will be appreciated that the material from which head receiver 120 and replaceable head 210 are formed will affect the above-described characteristics of replaceable head 210 as well as the optimum specifications (e.g., dimensions) of replaceable head 210, head receiver 120, and other components involved with engagement of replaceable head 210 with head receiver 120, particularly with regard to achieving the desired attachment/retention force. For instance, in the embodiment in which connectors 124 and 224 are provided with locking extensions 140, 240, respectively, locking extensions 140, 240 preferably are formed to remain securely engaged with each other during normal use. It will be appreciated that the dimensions of locking extensions 140, 240 of connectors 124, 224 in the form of dovetail connectors may be affected by the materials used to form head receiver 120, replaceable head 210, head-receiver-connector 124, and replaceable-head-connector 224. In addition, neck 114, head portion 116, and replaceable head 210 are preferably formed from materials that are perceived as comfortable in the user's mouth during use of toothbrush 100. Preferably, head portion 116 and replaceable head 210, and most preferably neck 114 as well, present smooth surfaces to the inside of the user's mouth. The materials of these components preferably are also selected to be perceived as comfortable for manually handling or manipulating replaceable head 210 with respect to head receiver 120. For instance, it is desirable that replaceable head 210 be sufficiently soft and flexible enough for the user to be able to easily detach and attach replaceable heads 210 on the harder head portion 116. As noted above, consumer preferences may be determined by various known testing methods and research.

A polypropylene resin such as HH315MO polypropylene sold by Borealis Compounds Inc. (see http://www.borealis-group.com/e-services/datasheet/results/download/?main=PP&sub=PP%20homopolymer&brand=HH315MO&reportType=1&specificationId=25117&country=US for material data sheet) has been found to be a suitable material for forming a bristle carrier 212 of replaceable head 210. Such resin has also been found to be suitable for forming, in particular, an AFT bristle carrier 212 (a bristle carrier with which anchor free technology has been used to couple bristles 215 thereto), particularly with regard to molding and achieving suitable tuft retention. Neck 114 and head 116 preferably are formed from an acetal polymer such as polyoxymethylene ("POM"), such as provided by Ticona Engineering Polymers (a subsidiary of Celanese Corporation). Other resins may be used, instead, which meet the various desired requirements for a toothbrush formed in accordance with principles of the present invention (e.g., vibration, stiffness, water resistance sealing, chemical resistance, head attachment, comfort, cost, etc.).

The nominal thickness of replaceable head 210 formed of HH315MO polypropylene (such as formed with AFT for connection of bristles 215 thereto) is approximately 8.7 mm, and preferably as thin as approximately 7.9 mm. For head receiver 120 and replaceable head 210 formed of POM and HH315MO polypropylene, respectively, locking extensions 140, 240 preferably are at least about 0.25 mm in depth and at least about 18 degrees from a normal to toothbrush-head-receiving surface 122 and head-receiver-engaging surface 222, respectively. It will be appreciated that such dimensions and geometry may be individually altered to achieve the desired engagement (such as, without limitation, by inter-locking) of replaceable head 210 and head receiver 120.

The exemplary embodiment illustrated in the figures has several separate and independent inventive features, which each, at least alone, has unique benefits which are desirable for, yet not critical to, the present invention. Therefore, the various separate features of the present invention need not all be present in order to achieve at least some of the desired characteristics and/or benefits of the present invention. One or more separate features may be combined, or only one of the various features need be present in a toothbrush formed in accordance with the principles of the present invention. Therefore, the present invention is not limited to only the embodiments specifically described herein. For instance, alignment of replaceable head 210 with head receiver 120 need not necessarily be achieved by alignment elements 130, 230, but may simply be achieved upon engagement of connectors 124, 224 with each other. It will further be appreciated that other forms of connectors may be used for connectors 124, 224. Preferably, the connectors used to engage replaceable head 210 with head receiver 120 are completely manual, and there is no need for the use of tools to achieve the engagement. However, other aspects of the present invention may be applied to replaceable heads with connectors that do require tools for engagement with and/or removal from the head receiver of a toothbrush main unit.

Moreover, throughout the present application, reference numbers are used to indicate a generic element or feature of the present invention. The same reference number may be used to indicate elements or features that are not identical in form, shape, structure, etc, yet which provide similar functions or benefits. Additional reference characters (such as letters, as opposed to numbers) may be used to differentiate similar elements or features from one another.

While the foregoing description and drawings represent exemplary embodiments of the present invention, it will be understood that various additions, modifications, and substitutions may be made therein without departing from the spirit and scope of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. For example, elements shown as integrally formed may be constructed of multiple parts or elements shown as multiple parts may be integrally formed, the operation of elements may be reversed or otherwise varied, the size or dimensions of the elements may be varied. The presently disclosed embodiments are therefore to be considered in all respects as illustrative and not restrictive, the scope of the invention being indicated by the appended claims, and not limited to the foregoing description.

In the claims, the term "comprises/comprising" does not exclude the presence of other elements or steps. Furthermore, although individually listed, a plurality of means, elements or method steps may be implemented by, e.g., a single unit or process. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality.

What is claimed is:

1. A replaceable toothbrush head for connection with a toothbrush main unit comprising a handle, a neck, and a head receiver extending along a longitudinal axis, the head receiver having a toothbrush-head-receiving surface with a first connector and a first alignment element, wherein said replaceable toothbrush head comprises:
    a plurality of bristles;
    a plate-like bristle carrier having a first surface from which said plurality of bristles extend, a second surface opposite said first surface and having a head-receiver-engaging surface for engaging and laying over the toothbrush-head-receiving surface in a substantially coplanar manner, and a longitudinal axis extending substantially parallel to said first surface and said second surface;
    a second connector extending on said head-receiver-engaging surface and shaped to engage the first connector; and
    a second alignment element associated with said head-receiver-engaging surface and shaped to engage the first alignment element axially along a rotation axis substantially perpendicular to said head-receiver-engaging surface and said bristle-carrier longitudinal axis to align said replaceable toothbrush head with respect to the head receiver for locking engagement of said second connector with the first connector;
    wherein:
    engagement of said second alignment element with the first alignment element stabilizes and aligns said replaceable toothbrush head with respect to the head receiver to permit rotation of said replaceable toothbrush head about said rotation axis to rotate said second connector between (i) a first position out of alignment with the first connector in which said replaceable toothbrush head is freely movable axially along said rotation axis and away from the head receiver, and (ii) a second position engaged with the first connector and locked against movement with respect to the first connector axially along said rotation axis to prevent removal of said replaceable toothbrush head from the head receiver axially along said rotation axis;
    said second connector is shaped and configured for entering into engagement with the first connector upon engagement of the first alignment element and said second alignment element with each other with said bristle carrier longitudinal axis transverse to the toothbrush main unit longitudinal axis, and for interlocking engagement with the first connector upon contacting said head-receiver-engaging surface with the toothbrush-head-receiving surface and upon rotation of said bristle carrier to align said bristle carrier longitudinal axis to be substantially parallel to the toothbrush main unit longitudinal axis and to place said second connector into a locked position in which said second connector is locked against axial movement along said rotation axis with respect to the first connector; and
    said replaceable toothbrush head is freely removable from the head receiver manually in an axial direction along said rotation axis without the use of a tool when said replaceable toothbrush head is rotated about said rotation axis from said locked position to said unlocked position.

2. A replaceable toothbrush head as in claim 1, wherein said head-receiver-engaging surface on said bristle carrier is substantially planar to engage a substantially planar toothbrush-head-receiving surface of the head receiver.

3. A replaceable toothbrush head as in claim 1, wherein said bristle carrier is elongated along said longitudinal axis thereof.

4. A replaceable toothbrush head as in claim 1, wherein said second alignment element comprises one of a projection sized and shaped to be received within a first alignment element in the form of an aperture, and an aperture sized and shaped to receive a first alignment element in the form of a projection.

5. A replaceable toothbrush head as in claim 1, wherein said second connector is in the form of a dovetail connector sized and shaped for engagement with a first connector in the form of a dovetail connector.

6. A replaceable toothbrush head as in claim 1, wherein said second connector is shaped and configured for axially unimpeded engagement with the first connector axially along said rotation axis upon engagement of the first alignment element and said second alignment element with each other.

7. A replaceable toothbrush head as in claim 1, wherein said bristle carrier is configured to generate a sound indicating interlocking engagement of said second connector with the first connector.

8. A replaceable toothbrush head for connection with a toothbrush main unit comprising a handle, a neck, and a head receiver extending along a longitudinal axis, the head receiver having a toothbrush-head-receiving surface with a first connector and a first alignment element, wherein said replaceable toothbrush head comprises:
   a plurality of bristles;
   a plate-like bristle carrier having a first surface from which said plurality of bristles extend and a second surface opposite said first surface and having a head-receiver-engaging surface for engaging and laying over the toothbrush-head-receiving surface in a substantially coplanar manner;
   a second connector extending on said head-receiver-engaging surface along a longitudinal axis of said bristle carrier and shaped to engage the first connector; and
   a second alignment element associated with said head-receiver-engaging surface and shaped to engage the first alignment element axially along a rotation axis substantially perpendicular to said head-receiver-engaging surface to align said replaceable toothbrush head with respect to the head receiver to engage said second connector with the first connector;
   wherein:
   engagement of said second alignment element with the first alignment element stabilizes and aligns said replaceable toothbrush head with respect to the head receiver to permit rotation of said replaceable toothbrush head about said rotation axis to engage said second connector with the first connector to prevent removal of said replaceable toothbrush head from the head receiver along said rotation axis;
   said second connector is shaped and configured for engagement with the first connector axially along said rotation axis upon engagement of the first alignment element and said second alignment element with each other with said bristle carrier longitudinal axis transverse to the toothbrush main unit longitudinal axis, and for interlocking engagement with the first connector upon contacting said head-receiver-engaging surface with the toothbrush-head-receiving surface and upon rotation of said bristle carrier to align said bristle carrier longitudinal axis to be substantially parallel to the toothbrush main unit longitudinal axis;
   said replaceable toothbrush head is removable from the head receiver manually without the use of a tool when said replaceable toothbrush head is rotated about said rotation axis from a locked position, with said replaceable toothbrush head longitudinal axis substantially aligned with the toothbrush main unit longitudinal axis and said second connector engaged with the first connector, to an unlocked position, with said replaceable toothbrush head longitudinal axis transverse to the toothbrush main unit longitudinal axis;
   the first alignment element is selected from the group consisting of an energy element, an optical lens, a teeth-cleaning element, and a toothpaste dispensing element; and
   said second alignment element comprises an aperture sized to receive the first alignment element.

9. A replaceable toothbrush head for connection with a toothbrush main unit comprising a handle, a neck, and a head receiver extending along a longitudinal axis, the head receiver having a toothbrush-head-receiving surface with a first connector and a first alignment element, wherein said replaceable toothbrush head comprises:
   a plurality of bristles;
   a plate-like bristle carrier having a first surface from which said plurality of bristles extend and a second surface opposite said first surface and having a head-receiver-engaging surface for engaging and laying over the toothbrush-head-receiving surface in a substantially coplanar manner;
   a second connector extending on said head-receiver-engaging surface along a longitudinal axis of said bristle carrier and shaped to engage the first connector; and
   a second alignment element associated with said head-receiver-engaging surface and shaped to engage the first alignment element axially along a rotation axis substantially perpendicular to said head-receiver-engaging surface to align said replaceable toothbrush head with respect to the head receiver to engage said second connector with the first connector;
   wherein:
   engagement of said second alignment element with the first alignment element stabilizes and aligns said replaceable toothbrush head with respect to the head receiver to permit rotation of said replaceable toothbrush head about said rotation axis to engage said second connector with the first connector to prevent removal of said replaceable toothbrush head from the head receiver along said rotation axis;
   said second connector is shaped and configured for engagement with the first connector axially along said rotation axis upon engagement of the first alignment element and said second alignment element with each other with said bristle carrier longitudinal axis transverse to the toothbrush main unit longitudinal axis, and for interlocking engagement with the first connector upon contacting said head-receiver-engaging surface with the toothbrush-head-receiving surface and upon rotation of said bristle carrier to align said bristle carrier longitudinal axis to be substantially parallel to the toothbrush main unit longitudinal axis;
   said replaceable toothbrush head is removable from the head receiver manually without the use of a tool when said replaceable toothbrush head is rotated about said rotation axis from a locked position, with said replaceable toothbrush head longitudinal axis substantially aligned with the toothbrush main unit longitudinal axis and said second connector engaged with the first connector, to an unlocked position, with said replaceable toothbrush head longitudinal axis transverse to the toothbrush main unit longitudinal axis; and
   said second connector is formed circumferentially about said second alignment element for rotational engagement with the first connector.

10. A toothbrush having a replaceable toothbrush head, said toothbrush comprising:
   a toothbrush main unit comprising:
      a handle;
      a neck; and
      a head receiver extending along a toothbrush-main-unit longitudinal axis, said head receiver having a toothbrush-head-receiving surface with a first connector and a first alignment element; and
   a replaceable toothbrush head comprising:
      a plurality of bristles;
      a plate-like bristle carrier having a first surface from which said plurality of bristles extend, a second surface opposite said first surface and having a head-receiver-engaging surface for engaging and laying over said toothbrush-head-receiving surface in a substantially coplanar manner, and a bristle-carrier longitudinal axis extending substantially parallel to said first surface and said second surface;

a second connector extending on said head-receiver-engaging surface and shaped to engage said first connector; and a second alignment element associated with said head-receiver-engaging surface and shaped to engage said first alignment element axially along a rotation axis substantially perpendicular to said head-receiver-engaging surface and said bristle-carrier longitudinal axis to align said replaceable toothbrush head with respect to said head receiver for engagement of said second connector with said first connector;

wherein:

engagement of said second alignment element with said first alignment element stabilizes and aligns said replaceable toothbrush head with respect to said head receiver to permit rotation of said replaceable toothbrush head about said rotation axis to rotate said second connector between (i) a first position out of alignment with said first connector in which said replaceable toothbrush head is freely movable axially along said rotation axis and away from said head receiver, and (ii) a second position engaged with said first connector and locked against movement with respect to said first connector axially along said rotation axis to prevent removal of said replaceable toothbrush head from said head receiver axially along said rotation axis;

said second connector is shaped and configured for entering into engagement with said first connector upon axial engagement of said first alignment element and said second alignment element with each other in an unlocked position with said bristle carrier longitudinal axis transverse to said toothbrush main unit longitudinal axis, and for interlocking engagement with said first connector upon contacting said head-receiver-engaging surface with said toothbrush-head-receiving surface and upon rotation of said bristle carrier to align said bristle carrier longitudinal axis to be substantially parallel to said toothbrush main unit longitudinal axis and to place said second connector into a locked position in which said second connector is locked against axial movement along said rotation axis with respect to the first connector; and said replaceable toothbrush head is freely removable from said head receiver manually in an axial direction along said rotation axis without the use of a tool when said replaceable toothbrush head is rotated about said rotation axis from said locked position to said unlocked position.

11. A toothbrush as in claim 10, wherein:

said first alignment element comprises one of a projection and an aperture;

said second alignment element comprises the other of a projection and an aperture; and said projection is sized and shaped to be received within said aperture.

12. A toothbrush as in claim 10, wherein said first and second connectors are in the form of dovetail connectors sized and shaped for engagement with each other.

13. A toothbrush as in claim 10, wherein said second connector is shaped and configured for axially unimpeded engagement with said first connector axially along said rotation axis upon engagement of said first alignment element and said second alignment element with each other.

14. A toothbrush as in claim 10, wherein said bristle carrier is configured to generate a sound indicating interlocking engagement of said second connector with said first connector.

15. A toothbrush as in claim 14, wherein said head-receiver-engaging surface of said bristle carrier is configured to generate a sound indicating interlocking engagement of said second connector with said first connector upon engagement with said toothbrush-head-receiving surface and rotation with respect to said toothbrush-head-receiving surface to place said second connector into interlocking engagement with said first connector.

16. A toothbrush having a replaceable toothbrush head, said toothbrush comprising:

a toothbrush main unit comprising:
  a handle;
  a neck; and
  a head receiver extending along a longitudinal axis, said head receiver having a toothbrush-head-receiving surface with a first connector and a first alignment element; and a replaceable toothbrush head comprising:
  a plurality of bristles;
  a plate-like bristle carrier having a first surface from which said plurality of bristles extend and a second surface opposite said first surface and having a head-receiver-engaging surface for engaging and laying over said toothbrush-head-receiving surface in a substantially coplanar manner;
  a second connector extending on said head-receiver-engaging surface along a longitudinal axis of said bristle carrier and shaped to engage said first connector; and a second alignment element associated with said head-receiver-engaging surface and shaped to engage said first alignment element axially along a rotation axis substantially perpendicular to said head-receiver-engaging surface to align said replaceable toothbrush head with respect to said head receiver to engage said second connector with said first connector;

wherein:

engagement of said second alignment element with said first alignment element stabilizes and aligns said replaceable toothbrush head with respect to said head receiver to permit rotation of said replaceable toothbrush head about said rotation axis to engage said second connector with said first connector to prevent removal of said replaceable toothbrush head from said head receiver along said rotation axis;

said second connector is shaped and configured for engagement with said first connector axially along said rotation axis upon engagement of said first alignment element and said second alignment element with each other with said bristle carrier longitudinal axis transverse to said toothbrush main unit longitudinal axis, and for interlocking engagement with said first connector upon contacting said head-receiver-engaging surface with said toothbrush-head-receiving surface and upon rotation of said bristle carrier to align said bristle carrier longitudinal axis to be substantially parallel to said toothbrush main unit longitudinal axis;

said replaceable toothbrush head is removable from said head receiver manually without the use of a tool when said replaceable toothbrush head is rotated about said rotation axis from a locked position, with said replaceable toothbrush head longitudinal axis substantially aligned with said toothbrush main unit longitudinal axis and said second connector engaged with said first connector, to an unlocked position, with said replaceable toothbrush head longitudinal axis transverse to said toothbrush main unit longitudinal axis;

said first alignment element is selected from the group consisting of an energy element, an optical lens, a teeth-cleaning element, and a toothpaste dispensing element; and said second alignment element comprises an aperture sized to receive said first alignment element.

17. A toothbrush having a replaceable toothbrush head, said toothbrush comprising:
   a toothbrush main unit comprising:
      a handle;
      a neck; and
      a head receiver extending along a longitudinal axis, said head receiver having a toothbrush-head-receiving surface with a first connector and a first alignment element; and
   a replaceable toothbrush head comprising:
      a plurality of bristles;
      a plate-like bristle carrier having a first surface from which said plurality of bristles extend and a second surface opposite said first surface and having a head-receiver-engaging surface for engaging and laying over said toothbrush-head-receiving surface in a substantially coplanar manner;
      a second connector extending on said head-receiver-engaging surface along a longitudinal axis of said bristle carrier and shaped to engage said first connector; and
      a second alignment element associated with said head-receiver-engaging surface and shaped to engage said first alignment element axially along a rotation axis substantially perpendicular to said head-receiver-engaging surface to align said replaceable toothbrush head with respect to said head receiver to engage said second connector with said first connector;
   wherein:
   engagement of said second alignment element with said first alignment element stabilizes and aligns said replaceable toothbrush head with respect to said head receiver to permit rotation of said replaceable toothbrush head about said rotation axis to engage said second connector with said first connector to prevent removal of said replaceable toothbrush head from said head receiver along said rotation axis;
   said second connector is shaped and configured for engagement with said first connector axially along said rotation axis upon engagement of said first alignment element and said second alignment element with each other with said bristle carrier longitudinal axis transverse to said toothbrush main unit longitudinal axis, and for interlocking engagement with said first connector upon contacting said head-receiver-engaging surface with said toothbrush-head-receiving surface and upon rotation of said bristle carrier to align said bristle carrier longitudinal axis to be substantially parallel to said toothbrush main unit longitudinal axis;
   said replaceable toothbrush head is removable from said head receiver manually without the use of a tool when said replaceable toothbrush head is rotated about said rotation axis from a locked position, with said replaceable toothbrush head longitudinal axis substantially aligned with said toothbrush main unit longitudinal axis and said second connector engaged with said first connector, to an unlocked position, with said replaceable toothbrush head longitudinal axis transverse to said toothbrush main unit longitudinal axis; and said second connector is formed circumferentially about said second alignment element for rotational engagement with said first connector.

18. A toothbrush having a replaceable toothbrush head, said toothbrush comprising:
   a toothbrush main unit comprising:
      a handle;
      a neck; and
      a head receiver extending along a longitudinal axis, said head receiver having a toothbrush-head-receiving surface with a first connector and a first alignment element; and
   a replaceable toothbrush head comprising:
      a plurality of bristles;
      a plate-like bristle carrier having a first surface from which said plurality of bristles extend and a second surface opposite said first surface and having a head-receiver-engaging surface for engaging and laying over said toothbrush-head-receiving surface in a substantially coplanar manner;
      a second connector extending on said head-receiver-engaging surface along a longitudinal axis of said bristle carrier and shaped to engage said first connector; and
      a second alignment element associated with said head-receiver-engaging surface and shaped to engage said first alignment element axially along a rotation axis substantially perpendicular to said head-receiver-engaging surface to align said replaceable toothbrush head with respect to said head receiver to engage said second connector with said first connector;
   wherein:
   engagement of said second alignment element with said first alignment element stabilizes and aligns said replaceable toothbrush head with respect to said head receiver to permit rotation of said replaceable toothbrush head about said rotation axis to engage said second connector with said first connector to prevent removal of said replaceable toothbrush head from said head receiver along said rotation axis;
   said second connector is shaped and configured for engagement with said first connector axially along said rotation axis upon engagement of said first alignment element and said second alignment element with each other with said bristle carrier longitudinal axis transverse to said toothbrush main unit longitudinal axis, and for interlocking engagement with said first connector upon contacting said head-receiver-engaging surface with said toothbrush-head-receiving surface and upon rotation of said bristle carrier to align said bristle carrier longitudinal axis to be substantially parallel to said toothbrush main unit longitudinal axis;
   said replaceable toothbrush head is removable from said head receiver manually without the use of a tool when said replaceable toothbrush head is rotated about said rotation axis from a locked position, with said replaceable toothbrush head longitudinal axis substantially aligned with said toothbrush main unit longitudinal axis and said second connector engaged with said first connector, to an unlocked position, with said replaceable toothbrush head longitudinal axis transverse to said toothbrush main unit longitudinal axis; and
   said head-receiver-engaging surface of said bristle carrier comprises one of a locking detent and locking recess engageable with the other of a locking detent and locking recess in said toothbrush-head-receiving surface of said head receiver.

19. A method of replacing the head of a toothbrush, the toothbrush having a handle, a neck, and a head receiver extending along a longitudinal axis, the head receiver having a toothbrush-head-receiving surface with a first connector and a first rotational alignment element, said method comprising:
- engaging a second rotational alignment element on a replaceable toothbrush head with the first rotational alignment element on the head receiver in a direction axially along a rotational axis substantially perpendicular to the toothbrush-head-receiving surface to stabilize and to align the replaceable toothbrush head with respect to the head receiver;
- engaging a head-receiver-engaging surface on a plate-like bristle carrier of the replaceable toothbrush head with the toothbrush-head-receiving surface with a longitudinal axis of the replaceable toothbrush head transverse to the longitudinal axis of the toothbrush;
- rotating the replaceable toothbrush head about the rotational axis to engage a second connector, on the replaceable toothbrush head, with the first connector;
- interlocking the second connector with the first connector upon substantially aligning the longitudinal axis of the replaceable toothbrush head with the longitudinal axis of the replaceable toothbrush head to be substantially coaxial with the longitudinal axis of the toothbrush to prevent relative axial movement of the first connector and the second connector thereby locking the replaceable toothbrush head on the toothbrush to prevent removal of the replaceable toothbrush head from the head receiver in a direction axially along the rotational axis; and
- rotating the replaceable toothbrush head about the rotational axis into a position with the longitudinal axis of the replaceable toothbrush head transverse to the longitudinal axis of the toothbrush to disengage the second connector from the first connector to permit removal of the replaceable toothbrush head from the head receiver manually in a direction axially along the rotational axis without the use of a tool.

20. A method of replacing the head of a toothbrush, the toothbrush having a handle, a neck, and a head receiver, all extending along a toothbrush longitudinal axis, the head receiver having a toothbrush-head-receiving surface with a first connector and a first rotational alignment element, said method comprising:
- engaging a second rotational alignment element on a replaceable toothbrush head with the first rotational alignment element on the head receiver to stabilize the replaceable toothbrush head with respect to the head receiver;
- engaging a head-receiver-engaging surface on a plate-like bristle carrier of the replaceable toothbrush head with the toothbrush-head-receiving surface with a longitudinal axis of the replaceable toothbrush head transverse to the toothbrush longitudinal axis;
- rotating the replaceable toothbrush head about the rotational axis to engage a second connector on the replaceable toothbrush head with the first connector;
- interlocking the second connector with the first connector upon substantially aligning the longitudinal axis of the replaceable toothbrush head to be substantially coaxial with the toothbrush longitudinal axis to prevent axial movement of the second connector relative to the first connector to prevent removal of the replaceable toothbrush head from the head receiver; and
- rotating the replaceable toothbrush head about said rotational axis into a position with the longitudinal axis of the replaceable toothbrush head transverse to the toothbrush longitudinal axis to disengage the second connector from the first connector to permit axial removal of the replaceable toothbrush head from the head receiver manually without the use of a tool.

* * * * *